United States Patent

Mast et al.

[11] 3,986,833
[45] Oct. 19, 1976

[54] TEST COMPOSITION, DEVICE, AND METHOD FOR THE DETECTION OF PEROXIDATIVELY ACTIVE SUBSTANCES

[75] Inventors: Raymond L. Mast; Charles Tak Wai Lam, both of Elkhart, Ind.

[73] Assignee: Miles Laboratories, Inc., Elkhart, Ind.

[22] Filed: Sept. 8, 1975

[21] Appl. No.: 611,152

[52] U.S. Cl. .......................... 23/230 B; 23/253 TP; 252/408
[51] Int. Cl.² ........................................ G01N 33/16
[58] Field of Search ............... 23/230 B, 253 TP; 252/408

[56] References Cited

UNITED STATES PATENTS

| | | |
|---|---|---|
| 3,290,117 | 12/1966 | Adams, Jr. et al. ............ 23/230 B X |
| 3,506,404 | 4/1970 | Evans et al. ..................... 23/230 B |
| 3,654,179 | 4/1972 | Bauer ............................. 23/230 B X |
| 3,667,915 | 6/1972 | Klein ............................. 23/230 B |
| 3,853,472 | 12/1974 | Rittersdorf et al. ............ 23/230 B |

OTHER PUBLICATIONS

*Gradwohl's Clinical Laboratory Methods and Diagnosis,* 7th ed., vol. 2, Mosby & Co., St. Louis, (1970), pp. 1873–1874 relied upon.
*Merck Index,* 8th Ed., pp. 906–907, (1968).

Primary Examiner—Morris O. Wolk
Assistant Examiner—Timothy W. Hagan
Attorney, Agent, or Firm—Richard W. Winchell

[57] ABSTRACT

Improved test compositions, devices and methods are provided for detecting peroxidatively active substances in body fluids, excreta and the like. In the type of test compositions including an indicator capable of being oxidized in the presence of a peroxidatively active substance to provide a color change, an oxidizing agent effective to oxidize said indicator, and a potentiating agent, the improvement comprises the use as said potentiating agent of an acid salt or adduct of a compound selected from the class of compounds of the general formula

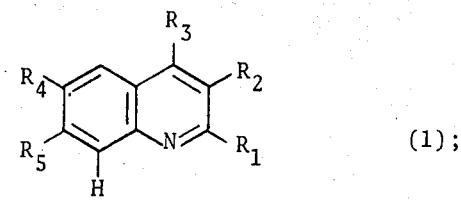

(1);

wherein $R_1$ is hydrogen, lower alkyl, hydroxy or thiophenyl; $R_2$ is hydrogen or lower alkyl; $R_3$ is hydrogen or lower alkyl; $R_4$ is hydrogen, carboxy, lower alkyl or lower alkoxy; and $R_5$ is hydrogen or lower alkyl.

19 Claims, No Drawings

TEST COMPOSITION, DEVICE, AND METHOD FOR THE DETECTION OF PEROXIDATIVELY ACTIVE SUBSTANCES

BACKGROUND OF THE INVENTION

The detection of small amounts of peroxidatively active substances, such as occult blood, hemoglobin, myoglobin, leukocytes, bacteria, etc., in body fluids and in body excreta has long been recognized as an invaluable aid to the medical practitioner in the diagnosis of many abnormal conditions. for example, blood is found in the gastric contents, in vomitus, in urine, and in feces in conditions often associated with erosion of the gastric and intestinal mucous membranes. In the urine, the presence of these peroxidatively active substances may be indicative of such abnormal conditions as typhus, scurvy, purpura, pyemia, nephritis, third degree burns, carcinogenic conditions, disease and infection of the urinary system, hemolytic toxins and post-cardiac infarct. Since peroxidatively active substances are usually not present in the body fluids or excreta in macroscopic amounts, it is often difficult to rapidly detect the presence of these substances by clinical methods alone, even by microscopic examination. Therefore, it is considered highly desirable to provide a sensitive, rapid and reliable test for these substances.

Various procedures, compositions and devices are described in the literature for the detection of occult peroxidatively active substances. For example, Kamlet in U.S. Pat. No. 2,290,436; Nicholls and Fonner in U.S. Pat. No 2,799,660; Fonner in U.S. Pat. No. 2,838,377; and Adams and Peterson in U.S. Pat. Nos. 3,012,976, 3,092,463, and 3,092,464, all assigned to the instant assignee, illustrate several test compositions which have been supplied to meet the need for a simple, reliable test for occult blood. These test compositions are based on the peroxidative or catalytic activity of the prosthetic groups present in blood. The peroxidatively active substances identified in hemoglobin belong to the general class of hemoproteins, conjugate proteins, all of which have the same prosthetic groups, iron protoporphyrin or heme. This prosthetic group has the ability to catalyze the transfer of oxygen from an oxygen source to an acceptor which in turn becomes oxidized. If the acceptor is a dye precursor, colorless until it becomes oxidized and colored in its oxidized form, then the presence of a peroxidatively acitvie substance is indicated by color formation. The rapidity of the color change and the depth or intensity of the color when compared to a set of standards is then a means for the quantitative estimation of the blood present.

Although the above mentioned compositions provide a rapid means for the detection of occult blood, the compositions are relatively insensitive to expecially minute quantities of peroxidatively active substances corresponding to blood dilutions of less than about 1:20,000, i.e., about 200 to 300 intact red blood cells per microliter of sample (RBC$\mu$/ 1). It has been determined by Adams et al. in U.S. Pat. No. 3,290,117 that the sensitivity of these occult blood test compositions can be markedly imporved and potentiated by the addition of quinoline or certain quinoline derivatives such as quinine. With the addition of these quinoline derivatives to the prior art occult blood compositions it is now possible to detect 5 to 50 RBC$\mu$/ 1. of sample which corresponds to a blood dilution as low as 1:1,000,000. Another approach, disclosed in U.S. Pat. No. 3,853,472, reports the use of fused polycyclic derivatives of quinoline as potentiating or activating agents with similar sensitivities.

Since the sensitivity of the prior art occult blood tests is of such great importance, it is essential that these tests not only be highly sensitive to peroxidatively active substances, but also be stable, ie., they must retain their sensitivity. Unfortunately, except for those improved compositions containing quinine or certain other quinoline derivatives, many of the highly sensitive prior art compositions are unstable due to the volatility of the added potentiators at room temperatures or temperatures slightly above. Furthermore, virtually all of the prior art compositions utilize potentiators which are water insoluble and require suspension in organic solvents prior to incorporation into a test composition. For instance, in commercial practice, the known potentiators must be suspended in an organic solvent solution containing the indicators. As a result, the indicators are often rapidly discolored in the presence of these potentiators and must be discarded. It would therefore be highly desirable to provide test compositions which are not only rapid and highly sensitive but are also capable of retaining their sensitivity without discoloring the indicator system.

SUMMARY OF THE INVENTION

In accordance with the present invention, improved test compositions, devices and methods for the detecting of peroxidatively active substances are provided which avoid the disadvantages of the prior art compositions discussed above. The test compositions include an indicator capable of being oxidized in the presence of peroxidatively active substances to provide a color change, an oxidizing agent effective to oxidize said indicator, and a potentiating agent. The potentiating agent comprises the acid salt or adduct of a compound selected from the class of compounds of the general formula

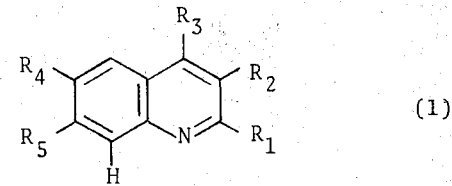

(1)

wherein $R_1$ is hydrogen, lower alkyl, hydroxy or thiophenyl; $R_2$ is hydrogen or lower alkyl; $R_3$ is hydrogen or lower alkyl; $R_4$ is hydrogen, carboxy, lower alkyl or lower alkoxy; and $R_5$ is hydrogen or lower alkyl. It is understood that the term "lower" refers to radicals containing up to four carbon atoms.

DESCRIPTION OF THE INVENTION

The compounds found to be satisfactory for use in the test compositions of this invention include the acid salts or adducts of the compounds of general formula (1) with most mineral or organic acids, provided the acid is capable of reacting with the compounds of general formula (1) to produce but one product, ie., the water soluble, acid salt or adduct compound. Suitable mineral acids capable of producing the adduct include hydrochloric, phosphoric, sulfuric and the like. Suitable organic acids include citric, malonic, sulfosalicylic, tartaric and the like. The compounds of general formula (1) which are most suitable in the improved compositions include the acid salts or adducts of quinoline substituted in the 4, 6, or 7 position. By way of specific example, the improved test compositions contain the acid salts or adducts of quinoline; 6-methoxyquinoline; 6-methylquinoline; 7-methylquinoline; 2,6-dimethylquinoline and 4,6-dimethylquinoline. Preferred compositions contain the acid salts or adducts of quinoline itself and 6-methoxyquinoline. Other useful compounds are quinoline sulfate; 6-methoxyquinoline sulfate; 6-methoxyquinoline hydrochloride; 6-methoxyquinoline phosphate; 6-methoxyquinoline malonate; 6-methoxyquinoline sulfosalicylic acid salt and 6-methoxyquinoline tartaric acid salt.

The acid salts or adducts described above are either commercially available or are easily prepared from commercially available materials. For instance, the acid salts or adducts are conveniently prepared by suspending a compound of general formula (1) in an organic solvent, such as ethanol, and adding thereto a sufficient quantity of one of the aforementioned mineral or organic acids. Almost immediately, a copious precipitate of the acid salt or adduct forms. The precipitate is then separated from the organic solvent, resuspended in fresh solvent to wash out excess acid, separated again and dried. Acid salts or adducts so prepared are easily identified by conventional methods and their sharp melting points indicate that they can be used without further purification.

The test compositions which are improved by incorporation of the acid salts or adducts described above contain at least an indicator and an oxidizing agent and may be prepared in a tablet form or incorporated with a carrier member or matrix such as an absorbent matrix. Suitable indicators are those capable of being oxidized in the presence of a peroxidatively active substance to provide a color change and include well known materials such as orthotolidine, orthotoluidine, paratoluidine, orthophenylenediamine, N,N'-dimethyl-p-phenylenediamine, N,N'-diethyl-p-phenylenediamine, benzidine, p-anisidine, di-anisidine, o-cresol, m-cresol, p-cresol, alpha-naphthol, beta-naphthol, catechol, guaiacol, pyrogallol or those of the heterocyclic azine series for example bis-(N-ethyl-quinol-2-one)-azine or (N-methylbenzthiazol-2-one)-(1-ethyl-3-phenyl-5-methtriazol-2-one)-azine. As oxidizing agents there can be used, for example cumene hydroperoxide, diisopropylbenzene hydroperoxide, paramethane hydroperoxide, 2,5-dimethylhexane-2,5-dihydroperoxide and other well known oxidizing agents effective to oxidize the indicators.

In a preferred embodiment, the improved test compositions of this invention are incorporated on or with a matrix and utilized as a dip and read test device. The test device may be prepared by various well known methods which include impregnating an absorbent matrix material with a solution or solutions of the test composition and thereafter drying the impregnated matrix, thus adhesively incorporating within the matrix a finely divided, intimate mixture of the ingredients and the like, Suitable absorbent matrices which may be used include paper, cellulose, wood, synthetic resin fleeces, glass fiber paper, polypropylene felt, nonwoven or woven fabrics and the like. The preferable mode of preparation is to impregnate the matrix in two separate steps. For instance, the matrix is first impregnated with an aqueous mixture containing at least an oxidizing agent and the acid salt or adduct of general formula (1) and then dried. The dried matrix is then impregnated with a second mixture containing at least an indicator and an organic solvent and is again dried. The dried impregnated matrix thusly prepared is advantageously affixed by suitable means to a carrier member for ease of use.

In addition to the above test composition components which actively participate in the test reaction, further components such as thickening agents, wetting agents, buffers, emulsifying agents and other well known adjuvants may also be included in the test composition or device of the present invention. Thus, for example, as thickening agents, there can be used various materials such as gelatin, algin, carrageenin, casein, albumin, methyl cellulose, polyvinylpyrrolidone, and the like. As wetting agents, it is preferable to use sodium laurylsulfate but any long chained organic sulfate or sulfonate, such as dioctyl sodium sulfosuccinate or sodium dodecyl-benzene sulphonate may also be used. For the buffering systems, there can be used tartarate, phosphate, phthalate, citrate, acetate, or succinate buffers. Preferably, the compositions are buffered to a pH value from about 4.0 to 7.0. As emulsifying agents, there can be used polyvinyl alcohol, gum arabic, carboxy vinyl polymers and the like. The organic solvents which are useful to suspend the indicator include most nonreactive, volatile solvents such as chloroform, ethylene dichloride, benzene, ethyl acetate and the like.

In use, the impregnated matrix of the test device is immersed in the fluid or liquid suspension of the material to be tested and immediately withdrawn. In the presence of a peroxidatively active substance, the test composition gives a positive color reaction. The color which results is then compared with precalibrated color standards for an estimation of the quantitative amount of peroxidatively active substance contained in the specimen. Intact peroxidatively active substances, such as intact red blood cells, appear as dots or flecks of color on the otherwise uncolored matrix. Hemolyzed peroxidatively active substances uniformly color the matrix and may be easily distinguished from intact peroxidatively active substances. In addition to visual comparison, various instrumental methods may also be employed to determine the quality of the color developed, thus increasing the accuracy of the test by obviating the subjective determination of color by the human eye.

It has been found that the improved test compositions and devices of this invention are not only stable, but are also highly sensitive. The instant test compositions are capable of detecting even individual intact peroxidatively active substances at concentrations as low as 5 to 50 RBC/$\mu$l of sample which corresponds to a blood dilution as low as 1:1,000,000. This high degree of sensitivity for test compositions incorporating the acid salts or adducts of the compounds of general formula (1) is indeed unexpected.

Due to the water solubility of the acid salts or adducts of the compounds of general formula (1), these compounds may be dispersed in aqueous suspensions. Thus in the preparation of the test compositions, direct contact, in solution, with the indicator, which requires organic solvent to dissolve, can be avoided. The potential for discoloring the indicator system is significantly reduced. The improved test compositions, as a result, are therefore more reliable than the prior art test compositions.

The following illustrative examples are provided to further describe the invention but are not intended to limit the scope of the invention.

EXAMPLE 1

This example illustrates a typical method for preparing an acid salt or adduct of the compounds of general formula (1) and the incorporation of an improved test composition with a carrier matrix.

Five grams of quinoline were suspended in about 50 ml. of absolute ethanol. To this solution were then added 2 ml. of concentrated sulfuric acid under mixing conditions. A copious white precipitate formed immediately and was separated from the solvent by filtration. The precipitate was resuspended in fresh ethanol, separated again and dried. The material so recovered was quinoline sulfate having a melting point of 130° C.

The following components were mixed, stepwise to provide a first impregnating solution.

| COMPONENT: | | QUANTITY |
|---|---|---|
| (1) | Gum Arabic | 15 grams |
| (2) | Gelatin | 0.5 grams |
| (3) | Sodium Lauryl Sulfate | 1.0 grams |
| (4) | Cumene Hydroperoxide | 3.0 ml. |
| (5) | Sodium Citrate | 8.92 grams |
| (6) | Citric Acid, Anhydrous | 1.86 grams |
| (7) | Quinoline Sulfate | 0.75 grams |
| (8) | Distilled water to give | 100.0 ml. |
| | pH of mix | 4.8 |

Whatman 3MM filter paper was impregnated with the above solution and dried at a temperature of about 100° C. until dried. The dried paper was then immersed in a second impregnating solution of 0.4 grams o-tolidine in 100 ml. of chloroform and dried at a temperature of about 50° C. for 5 to 10 minutes. The impregnated paper, which was white to cream in color, was then cut into 5 mm. by 5mm. square pieces which were each attached to a polystyrene sheet plastic carrier strip to form the improved test device.

To determine the sensitivity of the test composition, the matrix portion of the finished test devices was momentarily immersed in and withdrawn from urine samples containing various levels of intact red blood cells. The test composition was found to react with intact red blood cells to produce green-to-blue dots or flecks on the impregnated paper, thus indicating a positive reaction. This test composition was found to be sensitive down to a level of 2 to 5 intact red blood cells per microliter of urine which corresponds to a blood dilution of about 1:1,000,000. Similarly prepared test compositions were found to be equally sensitive to hemolyzed blood cells but reacted by uniformly coloring the impregnated paper.

EXAMPLE 2

Following the method for preparing the acid salt or adduct described in Example 1, 6-methoxyquinoline was suspended in ethanol and mixed with 50 ml. of ethanol containing 7 grams of sulfosalicylic acid. The precipitate which formed was similarly separated, washed and dried. The recovered material was identified as 6-methoxyquinoline sulfosalicylic acid salt having a melting point of 225° C.

Improved test compositions were then prepared in accordance with the description of Example 1, replacing the quinoline sulfate with 0.75 grams of 6-methoxyquinoline sulfosalicylic acid salt. The sensitivity to intact red blood cells and hemolyzed blood of test devices incorporated with this test composition was found to be of the same order as the test devices of Example 1.

EXAMPLE 3

In accordance with Example 1, improved test compositions were prepared by replacing the quinoline sulfate with one of the acid salts or adducts listed below:

| Acid salt or adduct | melting point |
|---|---|
| 6-Methoxyquinoline hydrochloride | 212° C. |
| 6-Methoxyquinoline phosphate | 180° C. |
| 6-Methoxyquinoline malonate | 116° C. |
| 6-Methoxyquinoline tartaric acid salt | 105° C. |
| 6-Methoxyquinoline sulfate | 215° C. |
| 6-Methylquinoline sulfate | 93° C. |
| 7-Methylquinoline sulfate | 92° C. |

The sensitivity to intact red blood cells and hemolyzed blood of test devices incorporated with each test composition was found to be of the same order as the test devices of Example 1.

What is claimed is:

1. A test composition for detection of peroxidatively active substances in body fluids, body excreta and the like, of the type including an indicator capable of being oxidized in the presence of a peroxidatively active substance to provide a color change, an oxidizing agent effective to oxidize said indicator, and a potentiating agent, wherein said potentiating agent comprises a water soluble acid salt or adduct of a compound selected from the class of compounds having the formula

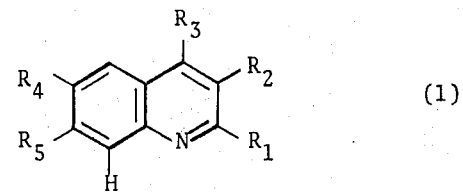

(1)

wherein $R_1$ is hydrogen, lower alkyl, hydroxy or thiophenyl; $R_2$ is hydrogen or lower alkyl; $R_3$ is hydrogen or lower alkyl; $R_4$ is hydrogen, carboxy, lower alkyl or lower alkoxy; and $R_5$ is hydrogen or lower alkyl.

2. A composition according to claim 1, wherein said acid salt or adduct is a mineral acid salt water soluble adduct.

3. A composition according to claim 1, wherein said water soluble acid salt or adduct is an organic acid salt or adduct.

4. A composition according to claim 1, wherein said compound is 6-methoxyquinoline.

5. A composition according to claim 4, wherein said potentiating agent is 6-methoxyquinoline sulfate.

6. A composition according to claim 4, wherein said potentiating agent is 6-methoxyquinoline hydrochloride.

7. A composition according to claim 4, wherein said potentiating agent is 6-methoxyquinoline phosphate.

8. A composition according to claim 4, wherein said potentiating agent is 6-methoxyquinoline malonate.

9. A composition according to claim 4, wherein said potentiating agent is 6-methoxyquinoline sulfosalicylic acid salt.

10. A composition according to claim 4, wherein said potentiating agent is 6-methoxyquinoline tartaric acid salt.

11. A composition according to claim 1, wherein said potentiating agent is a water soluble acid salt or adduct of quinoline.

12. A composition according to claim 11, wherein said potentiating agent is quinoline sulfate.

13. A composition according to claim 1, wherein said potentiating agent is a water soluble acid salt or adduct of 6-methylquinoline.

14. A composition according to claim 1, wherein said potentiating agent is a water soluble acid salt or adduct of 7-methylquinoline.

15. A composition according to claim 1, wherein said potentiating agent is a water soluble acid salt or adduct of 2,6-dimethylquinoline.

16. A composition according to claim 1, wherein said potentiating agent is a water soluble acid salt or adduct of 4,6-dimethylquinoline.

17. A test device for detecting peroxidatively active substances in body fluids, excreta and the like, of the type having a carrier matrix incorporated with an oxidizing agent, an indicator, and a potentiating agent wherein said potentiating agent comprises a water soluble acid salt or adduct of a compound selected from the class of compounds of the general formula

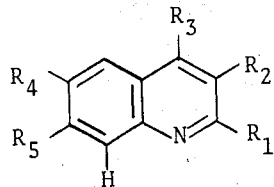
(1)

wherein $R_1$ is hydrogen, lower alkyl, hydroxy or thiophenyl; $R_2$ is hydrogen or lower alkyl; $R_3$ is hydrogen or lower alkyl; $R_4$ is hydrogen, carboxy, lower alkyl or lower alkoxy; and $R_5$ is hydrogen or lower alkyl.

18. A method for detecting minor amounts of a peroxidatively active substance in body fluids, excreta and the like, which comprises contacting a test sample of the body fluid or excreta with the carrier matrix of a test device as claimed in claim 17 and observing the color formation thereon as an indication of the presence of a peroxidatively active substance in said sample.

19. A method according to claim 18, wherein the peroxidatively active substance is occult blood.

* * * * *

UNITED STATES PATENT OFFICE
CERTIFICATE OF CORRECTION

PATENT NO. : 3,986,833
DATED : October 19, 1976
INVENTOR(S) : Raymond L. Mast *et al.*

It is certified that error appears in the above-identified patent and that said Letters Patent are hereby corrected as shown below:

Column 1, line 12, "for" should read --For--.

line 59, "(RBCμ/1.)" should read --(RBC/μl.)--.

line 62, "imporved" should read --improved--.

line 66, "(RBCμ/1.)" should read --(RBC/μl.)--.

Column 3, line 62, "like," should read --like.--.

Column 6, line 52, after "said" insert --water soluble--.

line 53, after "salt" delete "water soluble" and insert --or--.

Signed and Sealed this

Fourth Day of January 1977

[SEAL]

Attest:

RUTH C. MASON
*Attesting Officer*

C. MARSHALL DANN
*Commissioner of Patents and Trademarks*